(12) United States Patent
Quan et al.

(10) Patent No.: US 11,842,465 B2
(45) Date of Patent: Dec. 12, 2023

(54) SYSTEMS AND METHODS FOR MOTION CORRECTION IN MEDICAL IMAGING

(71) Applicant: SHANGHAI UNITED IMAGING HEALTHCARE CO., LTD., Shanghai (CN)

(72) Inventors: Guotao Quan, Shanghai (CN); Yi Wang, Shanghai (CN); Jiao Tian, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 128 days.

(21) Appl. No.: 17/100,820

(22) Filed: Nov. 21, 2020

(65) Prior Publication Data

US 2021/0158492 A1 May 27, 2021

(30) Foreign Application Priority Data

Nov. 21, 2019 (CN) .......................... 201911146934.5

(51) Int. Cl.
*G06T 7/20* (2017.01)
*G06T 5/00* (2006.01)
(Continued)

(52) U.S. Cl.
CPC ................ *G06T 5/005* (2013.01); *G06T 5/50* (2013.01); *G06T 7/0014* (2013.01); *G06T 7/20* (2013.01);
(Continued)

(58) Field of Classification Search
CPC ......... G06T 5/005; G06T 5/50; G06T 7/0014; G06T 7/20; G06T 2207/10016; G06T 2207/20081; G06T 2207/30048; G06T 5/003; G06T 2207/20084; G06T 2207/30061; G06T 11/008; A61B 5/055; A61B 6/5264; A61B 8/5276; A61B 6/03; A61B 6/032; A61B 6/037; A61B 6/4417; A61B 6/02; A61B 6/486; A61B 5/7214; G06N 3/084; G06N 3/0454

See application file for complete search history.

(56) References Cited

U.S. PATENT DOCUMENTS

2017/0196527 A1* 7/2017 Kokubun ............. A61B 6/5217
2018/0204358 A1* 7/2018 An ..................... G01R 33/0029
(Continued)

FOREIGN PATENT DOCUMENTS

CN    107945132 A    4/2018
WO    2019086337 A1   5/2019

*Primary Examiner* — Amandeep Saini
*Assistant Examiner* — Denise G Alfonso
(74) *Attorney, Agent, or Firm* — METIS IP LLC

(57) ABSTRACT

Systems and methods for motion correction in medical imaging are provided in the present disclosure. The systems may obtain at least two image sequences relating to a subject. Each of the at least two image sequences may be reconstructed based on image data that is acquired by a medical imaging device during one of at least two time periods. The subject may undergo a physiological motion during the at least two time periods. The systems may generate, based on the at least two image sequences, at least one corrected image sequence relating to the subject by correcting, using a motion correction model, an artifact caused by the physiological motion.

20 Claims, 8 Drawing Sheets

(51) Int. Cl.
*G06T 5/50* (2006.01)
*G06T 7/00* (2017.01)
*A61B 5/055* (2006.01)
*A61B 6/00* (2006.01)
*A61B 8/08* (2006.01)

(52) U.S. Cl.
CPC ............ *A61B 5/055* (2013.01); *A61B 6/5264* (2013.01); *A61B 8/5276* (2013.01); *G06T 2207/10016* (2013.01); *G06T 2207/20081* (2013.01); *G06T 2207/30048* (2013.01)

(56) References Cited

U.S. PATENT DOCUMENTS

| | | | |
|---|---|---|---|
| 2019/0147588 A1 | 5/2019 | Rowley Grant et al. | |
| 2021/0225047 A1* | 7/2021 | Pawar | A61B 5/7207 |
| 2022/0117508 A1* | 4/2022 | Dharmakumar | G01R 33/561 |

* cited by examiner

500

| Obtaining at least two image sequences relating to a subject, wherein each of the at least two image sequences corresponds to one of least two time periods and the subject undergoes a physiological motion during the at least two time periods | ⌇ 501 |

| Generating, based on the at least two image sequences, at least one corrected image sequence relating to the subject by correcting, using a motion correction model, an artifact caused by the physiological motion | ⌇ 503 |

701 — Obtaining a plurality of training samples each of which includes at least two sample image sequences relating to a sample subject and at least one gold standard image sequence corresponding to the at least two sample image sequences 703 — Generating a motion correction model by training a machine learning model using the plurality of training samples

FIG. 7

SYSTEMS AND METHODS FOR MOTION CORRECTION IN MEDICAL IMAGING

CROSS-REFERENCE TO RELATED APPLICATIONS

This application claims priority of Chinese Patent Application No. 201911146934.5, filed on Nov. 21, 2019, the contents of which are hereby incorporated by reference.

TECHNICAL FIELD

The disclosure generally relates to the field of medical image processing, and more particularly relates to systems and methods for motion correction in medical imaging.

BACKGROUND

In medical imaging or image processing, some factors may cause an artifact in an image of an object, which may reduce the image quality of the image. In some embodiments, the artifact may include a motion artifact. The motion artifact may be caused by a motion (e.g., a physical motion or a physiological motion) of the object during the imaging process. Taking the heart of a subject as an example, an image of the heart may include a motion artifact caused by a motion of the heart. A correction algorithm may be used for correcting a motion artifact in an image.

SUMMARY

In an aspect of the present disclosure, a system for motion correction in medical imaging are provided in the present disclosure. The system may include at least one storage device including a set of instructions and at least one processor configured to communicate with the at least one storage device. When executing the set of instructions, the at least one processor may be configured to direct the system to perform the following operations. The at least one processor may obtain at least two image sequences relating to a subject. Each of the at least two image sequences may be reconstructed based on image data that is acquired by a medical imaging device during one of at least two time periods. The subject may undergo a physiological motion during the at least two time periods. The at least one processor may generate, based on the at least two image sequences, at least one corrected image sequence relating to the subject by correcting, using a motion correction model, an artifact caused by the physiological motion.

In some embodiments, each of at least two image sequences may relate to the heart of the subject, and the physiological motion may include a cardiac motion.

In some embodiments, the physiological motion may include a motion cycle.

In some embodiments, a duration of each of the at least two time periods may be shorter than a duration of the motion cycle.

In some embodiments, the at least two image sequences may be acquired within a same motion cycle or different motion cycles.

In some embodiments, the obtaining at least two image sequences relating to a subject may include obtaining a plurality of image sequences relating to the subject, and determining the at least two image sequences from the plurality of image sequences, wherein the at least two image sequences satisfy a condition relating to a motion amplitude.

In some embodiments, the generating, based on the at least two image sequences, at least one corrected image sequence relating to the subject using a motion correction model may include determining at least two ranked image sequences by ranking, based on the at least two time periods, the at least two image sequences; inputting, according to the ranking of the at least two image sequences, the at least two ranked image sequences into the motion correction model; and outputting the at least one corrected image sequence by the motion correction model.

In some embodiments, 7, the at least two image sequences may be acquired within a same motion cycle. The determining at least two ranked image sequences by ranking, based on the at least two time periods, the at least two sample image sequences may include ranking, according to a chronological order of the at least two time periods, the at least two sample image sequences.

In some embodiments, the at least two image sequences may be acquired within different motion cycles. The determining at least two ranked image sequences by ranking, based on the at least two sample time periods, the at least two sample image sequences may include for each of the at least two time periods, determining a relative position of the time period with respect to its corresponding motion cycle; ranking, according to an order of the at least two relative positions, the at least two time periods; and ranking, according to the at least two ranked time periods, the at least two sample image sequences.

In some embodiments, the motion correction model may be obtained according to operations including obtaining a plurality of samples each of which may include at least two sample image sequences relating to a sample subject and at least one gold standard image sequence corresponding to the at least two sample image sequences and generating the motion correction model by training a machine learning model using the plurality of samples. Each of the at least two image sequences may be reconstructed based on image data acquired by the medical imaging device during one of at least two sample time periods. The at least one gold standard image sequence may have no motion artifact.

In another aspect of the present disclosure, a method for motion correction in medical imaging is provided. The method may be implemented on a computing device including at least one processor and at least one storage device. The method may include obtaining at least two image sequences relating to a subject. Each of the at least two image sequences may be reconstructed based on image data that is acquired by a medical imaging device during one of at least two time periods. The subject may undergo a physiological motion during the at least two time periods. The method may also include generating, based on the at least two image sequences, at least one corrected image sequence relating to the subject by correcting, using a motion correction model, an artifact caused by the physiological motion.

In some embodiments, the generating, based on the at least two image sequences, at least one corrected image sequence relating to the subject using a motion correction model may include determining at least two ranked image sequences by ranking, based on the at least two time periods, the at least two image sequences; inputting, according to the ranking of the at least two image sequences, the at least two ranked image sequences into the motion correction model; and outputting the at least one corrected image sequence by the motion correction model.

In some embodiments, the at least two image sequences may be acquired within a same motion cycle. The determining at least two ranked image sequences by ranking, based on the at least two time periods, the at least two sample image sequences may include ranking, according to a chronological order of the at least two time periods, the at least two sample image sequences.

In some embodiments, the at least two image sequences may be acquired within different motion cycles. The determining at least two ranked image sequences by ranking, based on the at least two sample time periods, the at least two sample image sequences may include for each of the at least two time periods, determining a relative position of the time period with respect to its corresponding motion cycle; ranking, according to an order of the at least two relative positions, the at least two time periods; and ranking, according to the at least two ranked time periods, the at least two sample image sequences.

In some embodiments, the motion correction model may be obtained according to operations including obtaining a plurality of samples each of which may include at least two sample image sequences relating to a sample subject and at least one gold standard image sequence corresponding to the at least two sample image sequences and generating the motion correction model by training a machine learning model using the plurality of samples. Each of the at least two image sequences may be reconstructed based on image data acquired by the medical imaging device during one of at least two sample time periods. The at least one gold standard image sequence may have no motion artifact.

In another aspect of the present disclosure, a system for generating a motion correction model is provided. The system may include at least one storage device including a set of instructions and at least one processor configured to communicate with the at least one storage device. When executing the set of instructions, the at least one processor may be configured to direct the system to perform the following operations. The at least one processor may obtain a plurality of samples each of which may include at least two sample image sequences relating to a sample subject and at least one gold standard image sequence corresponding to the at least two sample image sequences. Each of the at least two image sequences may be reconstructed based on image data acquired by a medical imaging device during one of at least two sample time periods. The sample subject may undergo a physiological motion during the at least two sample time periods. The at least one gold standard image sequence may have no artifact caused by the physiological motion. The at least one processor may generate the motion correction model by training a machine learning model using the plurality of samples.

In some embodiments, each of at least two sample image sequences may relate to the heart of a sample subject, and the physiological motion may include a cardiac motion.

In some embodiments, the physiological motion may include a motion cycle.

In some embodiments, a duration of each of the at least two sample time periods may be shorter than a duration of the motion cycle.

In some embodiments, the generating the motion correction model by training a machine learning model using the plurality of samples may include for each of the plurality of samples, ranking, according to the at least two sample time periods, the at least two sample image sequences, and generating the motion correction model by training the machine learning model using the at least two ranked image sequences and the at least one gold standard image sequence corresponding to each of the plurality of samples.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 5 is a flowchart illustrating an exemplary process for motion correction according to some embodiments of the present disclosure;

FIG. 7 is a flowchart illustrating an exemplary process for generating a motion correction model according to some embodiments of the present disclosure.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

Figure 2:
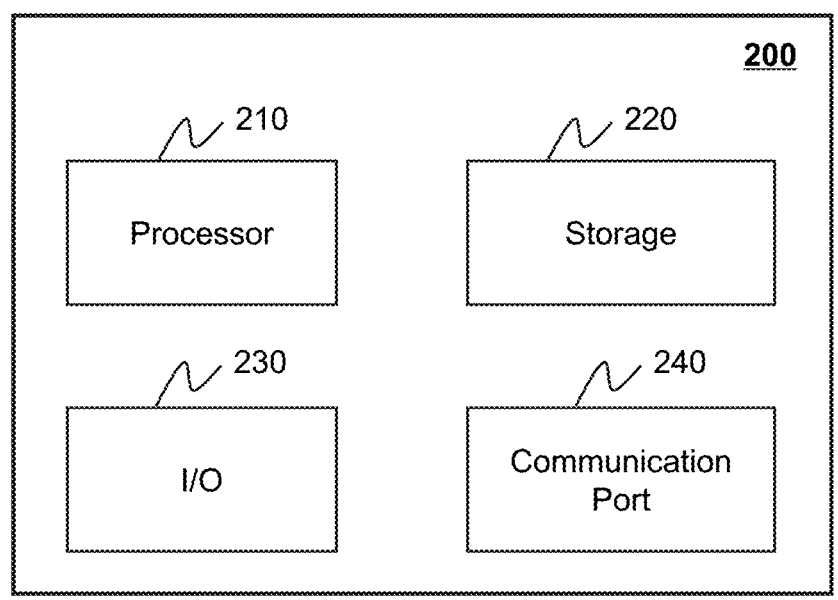
FIG. 2 is a schematic diagram illustrating hardware and/or software components of an exemplary computing device may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items. The term "image" in the present disclosure is used to collectively refer to image data (e.g., scan data) and/or images of various forms, including a two-dimensional (2D) image, a three-dimensional (3D) image, a four-dimensional (4D) image, etc. The term "pixel" and "voxel" in the present disclosure are used interchangeably to refer to an element of an image.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The term "imaging modality" or "modality" as used herein broadly refers to an imaging method or technology that gathers, generates, processes, and/or analyzes imaging information of a subject. The subject may include a biological subject (e.g., a human, an animal), a non-biological subject (e.g., a phantom), etc. In some embodiments, the subject may include a specific part, organ, and/or tissue of the subject. For example, the subject may include head, brain, neck, body, shoulder, arm, thorax, cardiac, stomach, blood vessel, soft tissue, knee, feet, or the like, or any combination thereof. The term "object" or "subject" are used interchangeably.

An aspect of the present disclosure relates to systems and methods for motion correction in medical imaging. The systems and methods may obtain at least two image sequences relating to a subject (e.g., the heart of a patient). Each of the at least two image sequences may be reconstructed based on image data that is acquired by a medical imaging device during one of at least two time periods. The subject may undergo a physiological motion (e.g., a cardiac motion) during the at least two time periods. The systems and the methods may generate, based on the at least two image sequences, at least one corrected image sequence relating to the subject by correcting, using a motion correction model (e.g., a trained deep learning model), an artifact caused by the physiological motion.

According to some embodiments of the present disclosure, the systems and methods may rank at least two image sequences according to an order of the at least two time periods. The systems and methods may input the at least two ranked image sequences into the motion correction model and output the at least one corrected image sequence. During traditional motion correction algorithm, image data acquired during a scan of the subject may need to be reconstructed; the reconstructed image sequences may be segmented and determine a motion trajectory of the subject; and the motion trajectory of the subject may be used for motion correction, which is complex and time-consuming. In comparison with the traditional motion correction algorithm, the correction process using the motion correction model may reconstruct a portion of the image data acquired during the scan and directly output a corrected image sequence by inputting reconstructed image sequences into the motion correction model, which can improve an efficiency of the motion correction and reduce a computing complexity of the motion correction. Moreover, the motion correction model may be trained based on data from a plurality of sample objects, which can better account for differences in different objects and improve the accuracy of the motion correction.

Figure 1:
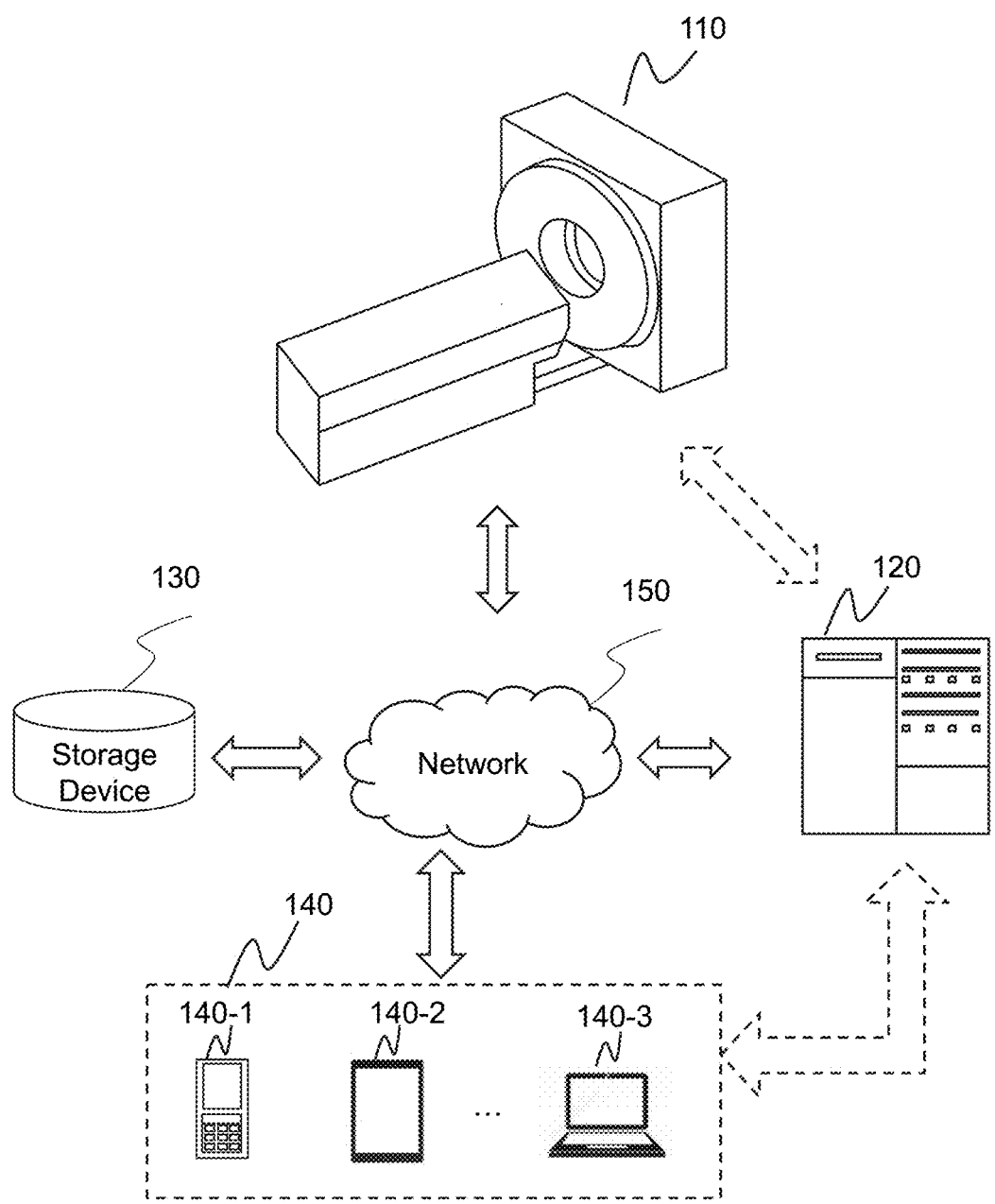
FIG. 1 is a schematic diagram illustrating an exemplary imaging system according to some embodiments of the present disclosure.

FIG. 1 is a schematic diagram illustrating an exemplary imaging system 100 according to some embodiments of the present disclosure. In some embodiments, the imaging system may be configured for non-invasive biomedical imaging (e.g., cardiac imaging, lung imaging), such as for disease diagnostic, treatment, and/or research purposes. In some embodiments, the imaging system may include a single modality imaging system and/or a multi-modality imaging system. The single modality imaging system may include, for example, an X-ray imaging system, a computed tomography (CT) system (e.g., a spiral CT system, a cone-beam CT system, etc.), a single photon emission computed tomography (SPECT) system, a digital radiography (DR) system, an ultrasonic imaging system, a positron emission tomography (PET) system, a magnetic resonance imaging (MRI) system, or the like, or any combination thereof. The multi-modality imaging system may include, for example, a PET-CT system, an X-ray-MRI system, a SPECT-MRI system, an image-guided radiotherapy system (e.g., a CT guided radiotherapy system), etc. It should be noted that the imaging system described below is merely provided for illustration purposes, and not intended to limit the scope of the present disclosure.

In some embodiments, the imaging system 100 may include modules and/or components for performing imaging and/or related analysis. Merely by way of example, as illustrated in FIG. 1, the imaging system 100 may include a medical imaging device 110, a processing device 120, a storage device 130, one or more terminals 140, and a network 150. The components in the imaging system 100 may be connected in various ways. Merely by way of example, the medical imaging device 110 may be connected to the processing device 120 through the network 150 or directly as illustrated in FIG. 1. As another example, the terminal(s) 140 may be connected to the processing device 120 via the network 150 or directly as illustrated in FIG. 1.

The medical imaging device 110 may be configured to acquire imaging data relating to a subject. The imaging data relating to a subject may include an image (e.g., an image slice), projection data, or a combination thereof. In some embodiments, the imaging data may be two-dimensional (2D) imaging data, three-dimensional (3D) imaging data, four-dimensional (4D) imaging data, or the like, or any combination thereof. In some embodiments, the medical imaging device 110 may include a CT device, an X-ray imaging device, a DR device, a SPECT device, an ultrasonic imaging device, a PET device, an MRI device, a PET-CT device, an X-ray-MRI device, a SPECT-MRI device, an image-guided radiotherapy device (e.g., a CT guided radiotherapy device), etc. The following descriptions are provided with reference to the medical imaging device 110 being a CT device. It is understood that this is for illustration purposes and not intended to be limiting. In some embodiments, the medical imaging device 110 may include a radiation source, a detector, a gantry, a table, etc. The radiation source and the detector may be mounted on the gantry. The subject may be placed on the table and moved to an imaging region of the imaging device. The radiation source may include a tube configured to emit radioactive rays (e.g., X rays) traveling toward the subject. The detector may detect radiation (e.g., X-rays) emitted from the imaging region of the medical imaging device 110. In some embodiments, the detector may include one or more detector units. The detector unit(s) may include a scintillation detector (e.g., a cesium iodide detector, a gadolinium oxysulfide detector), a gas detector, etc. The detector unit(s) may include a single-row detector and/or a multi-rows detector.

The processing device 120 may process data and/or information obtained from the medical imaging device 110, the terminal(s) 140, and/or the storage device 130. For example, the processing device 120 may generate a corrected image sequence by inputting at least two image sequences according to a specific time order into a motion correction model. As another example, the processing device 120 may train the motion correction model using a plurality of samples. Each of the plurality of samples may include at least two sample image sequences relating to a sample subject and at least one sample gold standard image sequence corresponding to the at least two sample image sequences.

In some embodiments, the generation and/or updating of the motion correction model may be performed on a processing device, while the application of the motion correction model may be performed on a different processing device. In some embodiments, the generation and/or updating of motion correction model may be performed on a processing device of a system different from the imaging system 100 or a server different from a server including the processing device 120 on which the application of motion correction model is performed. For instance, the generation and/or updating of motion correction model may be performed on a first system of a vendor who provides and/or maintains such a motion correction model and/or has access to training samples used to generate motion correction model, while motion correction based on the provided motion correction model may be performed on a second system of a client of the vendor. In some embodiments, the generation and/or updating of motion correction model may be performed on a processing device, while the application of motion correction model may be performed on a different processing device. In some embodiments, the generation and/or updating of motion correction model may be performed online in response to a request for motion correction. In some embodiments, the generation and/or updating of motion correction model may be performed offline.

In some embodiments, the motion correction model may be generated and/or updated (or maintained) by, e.g., the manufacturer of the medical imaging device 110 or a vendor. For instance, the manufacturer or the vendor may load the motion correction model into the imaging system 100 or a portion thereof (e.g., the processing device 120) before or during the installation of the medical imaging device 110 and/or the processing device 120, and maintain or update the motion correction model from time to time (periodically or not). The maintenance or update may be achieved by installing a program stored on a storage device (e.g., a compact disc, a USB drive, etc.) or retrieved from an external source (e.g., a server maintained by the manufacturer or vendor) via the network 150. The program may include a new model (e.g., a new motion correction model) or a portion of a model that substitute or supplement a corresponding portion of the model.

In some embodiments, the processing device 120 may be a computer, a user console, a single server or a server group, etc. The server group may be centralized or distributed. In some embodiments, the processing device 120 may be local or remote. For example, the processing device 120 may access information and/or data stored in the medical imaging device 110, the terminal(s) 140, and/or the storage device 130 via the network 150. As another example, the processing device 120 may be directly connected to the medical imaging device 110, the terminal(s) 140, and/or the storage device 130 to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

The storage device 130 may store data, instructions, and/or any other information. In some embodiments, the storage device 130 may store data obtained from the medical imaging device 110, the terminal(s) 140 and/or the processing device 120. For example, the storage device 130 may store image data acquired by the medical imaging device 110 during at least two time periods. As another example, the storage device 130 may store at least two image sequences relating to a subject. As still another example, the storage device 130 may store a motion correction model for motion correction. As further another example, the storage device 130 may store a plurality of samples for training the motion correction model. In some embodiments, the storage device 130 may store data and/or instructions that the processing device 120 may execute or use to perform exemplary methods/systems described in the present disclosure. In some embodiments, the storage device 130 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memories may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the imaging system 100 (e.g., the processing device 120, the terminal(s) 140, etc.). One or more components in the imaging system 100 may access the data or instructions stored in the storage device 130 via the network 150. In some embodiments, the storage device 130 may be directly connected to or communicate with one or more other components in the imaging system 100 (e.g., the processing device 120, the terminal(s) 140, etc.). In some embodiments, the storage device 130 may be part of the processing device 120.

In some embodiments, a user (e.g., a doctor, a technician, or an operator) may interact with the imaging system 100 through the terminal (s) 140. For example, a corrected image sequence determined after motion correction may be displayed on an interface of the terminal 140. The user may perform a user operation to provide feedback on whether the corrected image sequence satisfies an image quality. In some embodiments, the terminal(s) 140 may include a mobile device 140-1, a tablet computer 140-2, a laptop computer 140-3, or the like, or any combination thereof. In some embodiments, the mobile device 140-1 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 140 may be part of the processing device 120.

The network 150 may include any suitable network that can facilitate the exchange of information and/or data for the imaging system 100. In some embodiments, one or more components of the medical imaging device 110 (e.g., a CT device), the terminal(s) 140, the processing device 120, the storage device 130, etc., may communicate information and/or data with one or more other components of the imaging system 100 via the network 150. For example, the processing device 120 may obtain at least two image sequences and/or a motion correction model from the storage device 130 via the network 150. As another example, the processing device 120 may obtain user instructions from the terminal(s) 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the imaging system 100 may be connected to the network 150 to exchange data and/or information.

In some embodiments, the imaging system 100 may further include a physiological motion detection device (not shown) configured to acquire/detect a physiological motion of the subject. For example, the physiological motion detection device may acquire information of the physiological motion of the subject before, when, and/or after a scan is performed on the subject by the medical imaging device 110. In some embodiments, the physiological motion detection device may include a medical monitor device (e.g., an electrocardiograph (ECG) monitor), or a mobile device (e.g., a smart device, a wearable device, etc.) which may be installed with an application to record the physiological motion of the subject. In some embodiments, the detection device may be operably connected to the network 150 to communicate with one or more components of the imaging system 100. One or more components of the imaging system 100 may access data/information from the detection device via the network 150. In some embodiments, the detection device may be directly connected to or communicate with one or more components of the imaging system 100 (e.g., the processing device 120, the terminal(s) 140, etc.). In some embodiments, the detection device may be external to the imaging system 100 but communicate with the imaging system 100 (e.g., via the network 150).

It should be noted that the above description of the imaging system 100 is merely provided for the purposes of illustration, and not intended to limit the scope of the present disclosure. For persons having ordinary skills in the art, multiple variations and modifications may be made under the teachings of the present disclosure. For example, the imaging system 100 may include one or more additional components and/or one or more components of the imaging system 100 described above may be omitted. Additionally or alternatively, two or more components of the imaging system 100 may be integrated into a single component. A component of the imaging system 100 may be implemented on two or more sub-components.

FIG. 2 is a schematic diagram illustrating hardware and/or software components of an exemplary computing device 200 may be implemented according to some embodiments of the present disclosure. The computing device 200 may be used to implement any component of the imaging system as described herein. For example, the processing device 120 and/or a terminal 140 may be implemented on the computing device 200, respectively, via its hardware, software program, firmware, or a combination thereof. Although only one such computing device is shown, for convenience, the computer functions relating to the imaging system 100 as described herein may be implemented in a distributed fashion on a number of similar platforms, to distribute the processing load. As illustrated in FIG. 2, the computing device 200 may include a processor 210, storage 220, an input/output (I/O) 230, and a communication port 240.

The processor 210 may execute computer instructions (program codes) and perform functions of the processing device 120 in accordance with techniques described herein. The computer instructions may include, for example, routines, programs, objects, components, signals, data structures, procedures, modules, and functions, which perform particular functions described herein. In some embodiments, the processor 210 may perform instructions obtained from the terminal(s) 140. In some embodiments, the processor 210 may include one or more hardware processors, such as a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the medical imaging device 110, the terminal(s) 140, the storage device 130, or any other component of the imaging system 100. In some embodiments, the storage 220 may include a mass storage device, a removable storage device, a volatile read-and-write memory, a read-only memory (ROM), or the like, or any combination thereof. In some embodiments, the storage 220 may store one or more programs and/or instructions to perform exemplary methods described in the present disclosure.

The I/O 230 may input or output signals, data, and/or information. In some embodiments, the I/O 230 may enable user interaction with the processing device 120. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected with a network (e.g., the network 150) to facilitate data communications. The communication port 240 may establish connections between the processing device 120 and the medical imaging device 110, the terminal(s) 140, or the storage device 130. The connection may be a wired connection, a wireless connection, or a combination of both that enables data transmission and reception. The wired connection may include an electrical cable, an optical cable, a telephone wire, or the like, or any combination thereof. The wireless connection may include a Bluetooth network, a Wi-Fi network, a WiMax network, a WLAN, a ZigBee network, a mobile network (e.g., 3G, 4G, 5G, etc.), or the like, or any combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
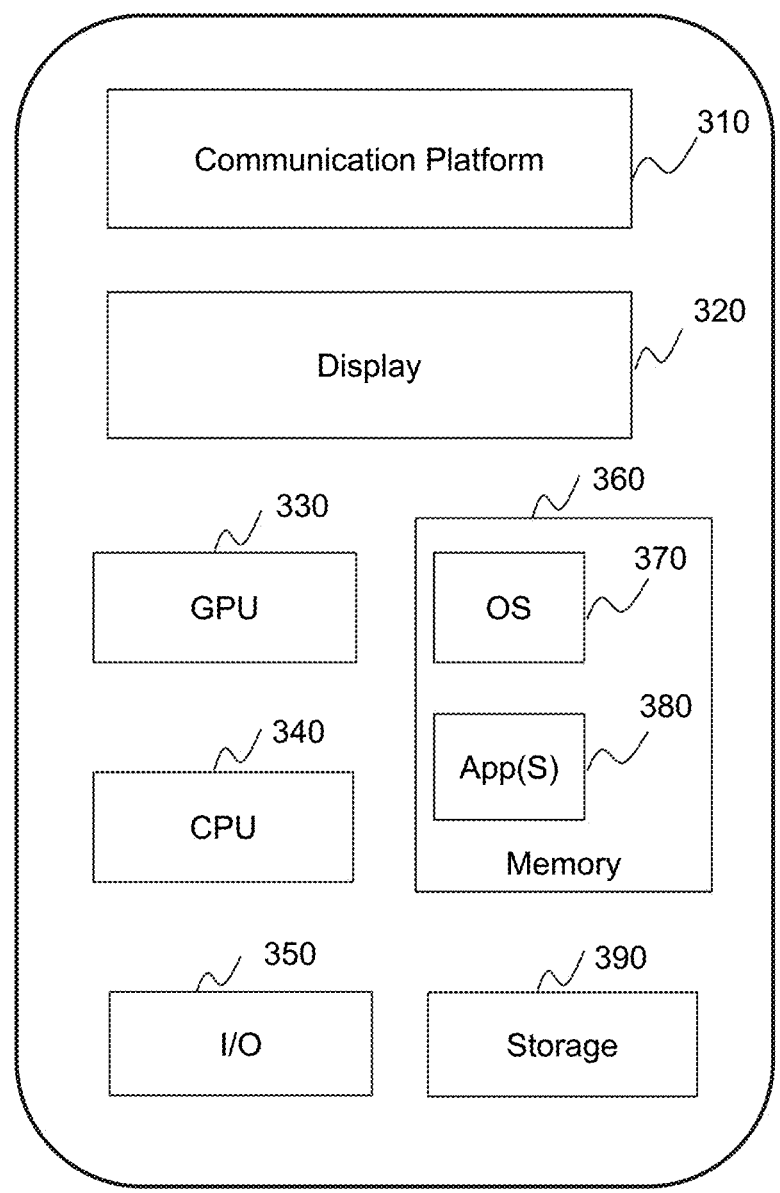
FIG. 3 is a schematic diagram illustrating hardware and/or software components of an exemplary mobile device according to some embodiments of the present disclosure.

FIG. 3 is a schematic diagram illustrating hardware and/or software components of an exemplary mobile device 300 according to some embodiments of the present disclosure. In some embodiments, one or more components (e.g., a terminal 140 and/or the processing device 120) of the imaging system 100 may be implemented on the mobile device 300.

As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 120. User interactions with the information stream may be achieved via the I/O 350 and provided to the processing device 120 and/or other components of the imaging system 100 via the network 150.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate an image as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4A:
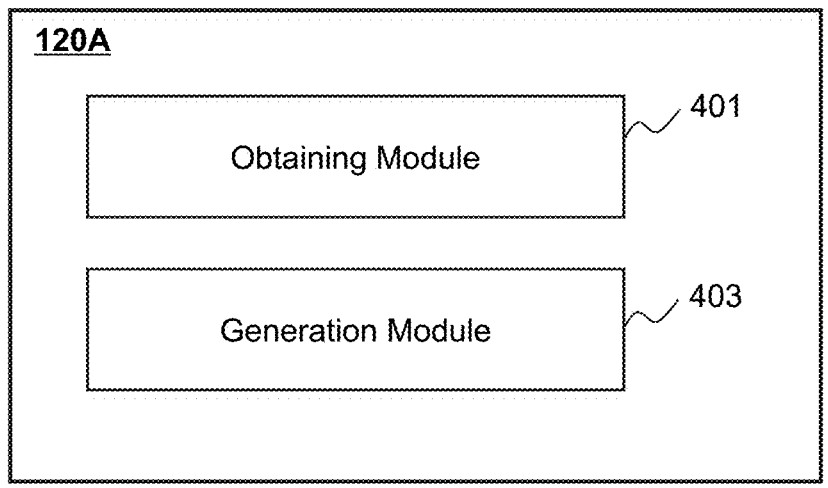
FIG. 4A and FIG. 4B are block diagrams illustrating exemplary processing devices according to some embodiments of the present disclosure.
Figure 4B:
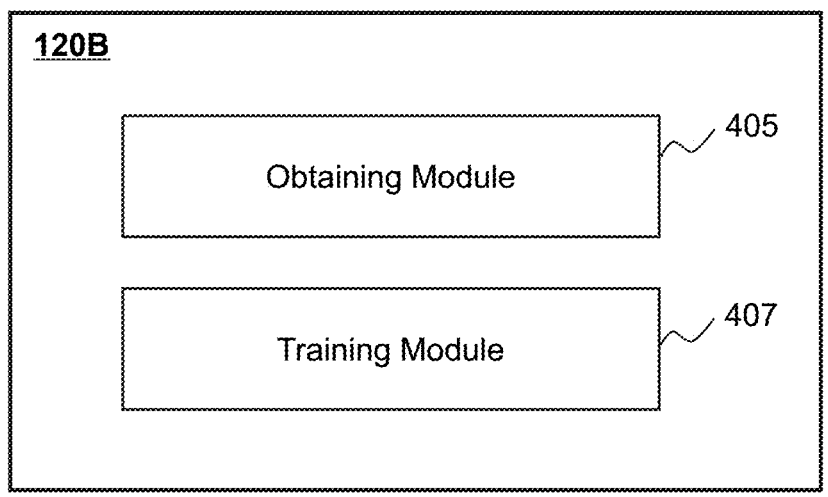

FIG. 4A and FIG. 4B are block diagrams illustrating exemplary processing devices 120A and 120B according to some embodiments of the present disclosure. In some embodiments, the processing devices 120A and 120B may be embodiments of the processing device 120 as described in connection with FIG. 1. In some embodiments, the processing devices 120A and 120B may be respectively implemented on a processing unit (e.g., the processor 210 illustrated in FIG. 2 or the CPU 340 as illustrated in FIG. 3). Merely by way of example, the processing devices 120A may be implemented on a CPU 340 of a terminal device, and the processing device 120B may be implemented on a computing device 200. Alternatively, the processing devices 120A and 120B may be implemented on a same computing device 200 or a same CPU 340. For example, the processing devices 120A and 120B may be implemented on a same computing device 200.

As shown in FIG. 4A, the processing device 120A may include an obtaining module 401 and a generation module 403.

The obtaining module 401 may be configured to obtain information/data from one or more components of the imaging device 100. For example, the obtaining module 401 may obtain a plurality of image sequences relating to the subject. Each of the plurality of image sequences may correspond to one of a plurality of time periods. The obtaining module 401 may obtain at least two image sequences relating to the subject from the plurality of image sequences. Each of the at least two sequences may correspond to one of least two time periods (also referred to as at least two first time periods). The subject may undergo a physiological motion (e.g., a cardiac motion) during the plurality of time periods. As another example, the obtaining module 401 may obtain physiological motion data (e.g., an ECG image) relating to the subject that is detected during the plurality of time periods. More descriptions regarding the obtaining of the at least two sequences and the physiological motion data may be found elsewhere in the present disclosure (e.g., operation 501 om FIG. 5 and the description thereof).

The generation model 403 may be configured to generate at least one corrected image sequence relating to the subject based on the at least two image sequences. For example, the generation module 403 may generate the at least one corrected image sequence by using a motion correction model. As used herein, a motion correction model refers to a machine learning model (e.g., a deep learning model) configured for motion artifact correction based on at least two image sequences and time information thereof. In some embodiments, the generation module 403 may determine at least two ranked image sequences by ranking, based on the at least two time periods, the at least two image sequences. The generation module 403 may input the at least two ranked image sequences, according to the ranking of the at least two image sequences, into the motion correction model. The generation module 403 may output the at least one image sequence by the motion correction model. More descriptions regarding the generation of the at least one corrected image may be found elsewhere in the present disclosure (e.g., operation 503 in FIG. 5 and the description thereof).

As shown in FIG. 4B, the processing device 120B may include an obtaining module 405 and a training module 407.

The obtaining module 405 may be configured to obtain data/information that can be used in training the motion correction model. For example, the obtaining module 405 may obtain a plurality of training samples. Each of the plurality of training samples may include at least two sample image sequences relating to a sample subject and at least one gold standard image sequence corresponding to the at least two sample image sequences. More descriptions regarding the obtaining of the plurality of training samples may be found elsewhere in the present disclosure (e.g., operation 701 in FIG. 7 and the description thereof).

The training module 407 may be configured to generate the motion correction model. For example, the training module 407 may generate the motion correction model by training a machine learning model using the plurality of samples. In some embodiments, the machine learning model may include a deep learning model. The deep learning model may include a neural network model, such as a U-NET model (e.g., a residual U-NET model, a dense U-NET model), a V-NET model, a super-resolution convolutional neural network (SRCNN) model, etc. In some embodiments, the training module 407 may divide the plurality of training samples into a first portion and a second portion (e.g., randomly). The first portion may be used to train the machine learning model to obtain the motion correction model. The second portion may be used to test the motion correction model to determine whether the motion correction model is satisfactory. In some embodiments, a ratio of a count (or number) of the first portion and a count (or number) of the second portion may be 8:2, 9:1, 9.5:0.5, etc. More descriptions regarding the training of the motion correction model may be found elsewhere in the present disclosure (e.g., operation 703 in FIG. 7 and the description thereof).

It should be noted that the above description is merely provided for the purposes of illustration, and not intended to limit the scope of the present disclosure. Apparently, for persons having ordinary skills in the art, multiple variations and modifications may be conducted under the teachings of the present disclosure. However, those variations and modifications do not depart from the scope of the present disclosure. Each of the modules described above may be a hardware circuit that is designed to perform certain actions, e.g., according to a set of instructions stored in one or more storage media, and/or any combination of the hardware circuit and the one or more storage media.

In some embodiments, the processing device 120A and/or the processing device 120B may be integrated and implemented on a same server and/or share two or more of the modules. For instance, the processing devices 120A and 120B may share a same obtaining module; that is, the obtaining module 401 and the obtaining module 405 are a same module. In some embodiments, any one of the modules in the processing device 120A or 120B may be divided into two or more units. In some embodiments, the processing device 120A and/or the processing device 120B may include one or more additional modules, such as a storage module (not shown) for storing data.

FIG. 5 is a flowchart illustrating an exemplary process for motion correction according to some embodiments of the present disclosure. In some embodiments, process 500 may be implemented as a set of instructions (e.g., an application) stored in a storage device (e.g., the storage device 130, the storage 220, and/or the storage 390). The processing device 120A (e.g., the processor 210, the CPU 340, and/or one or more modules illustrated in FIG. 4A) may execute the set of instructions, and when executing the instructions, the processing device 120A may be configured to perform the process 500. The operations of the illustrated process presented below are intended to be illustrative. In some embodiments, the process 500 may be accomplished with one or more additional operations not described and/or without one or more of the operations discussed. Additionally, the order of the operations of process 500 illustrated in FIG. 5 and described below is not intended to be limiting.

In some embodiments, when a medical imaging device (e.g., the medical imaging device 110) performs a scan on a subject (e.g., the heart or the lung of a patient), the subject may undergo a physiological motion (e.g., a cardiac motion, a respiratory motion, etc.) during the scan, which may cause a motion artifact (e.g., a cardiac motion artifact, a respiratory motion artifact, etc.). Traditionally, to generate a motion artifact-free image sequence relating to the subject, among the image data acquired during the scan, only a portion thereof acquired when the subject undergoes a minimal physiological motion is used for image reconstruction. Alternatively, a plurality of image sequences may be reconstructed based on the image data acquired during the scan. The plurality of image sequences may be segmented. The plurality of segmented image sequences may be registered to determine a motion trajectory of the subject (e.g., the heart or the lung of the patient) during the scan. The motion trajectory may be used to correct the motion artifact. However, the aforementioned traditional technologies may be time-consuming and/or the application thereof may be limited in complex conditions of the physiological motion (e.g., a condition of arrhythmia). In some embodiments, the process 500 may be performed for motion correction more efficiently and accurately. For illustration purposes, the process 500 is described with reference to a scan associated with a heart (also referred to as a cardiac scan). It should be noted that the process 500 is appliable to scanning of another portion of a subject during which the subject may undergo a physiological motion thereby causing a motion artifact.

In 501, the processing device 120A (e.g., the obtaining module 401) may obtain at least two image sequences relating to a subject (e.g., the heart of the patient). Each of the at least two image sequences may correspond to one of least two time periods (also referred to as at least two first time periods). The subject may undergo a physiological motion (e.g., a cardiac motion) during the at least two time periods.

In some embodiments, the medical imaging device 110 (e.g., a CT device) may perform a scan on the subject during a plurality of time periods to acquire a plurality of image data sets. Each of the plurality of image data sets may be acquired during one of the plurality of time periods. That is, during each of the plurality of time periods, the medical imaging device 110 may rotate its radiation source by multiple gantry angles to acquire multiple image data sub-sets relating to the subject. Each of the multiple image data sub-sets may correspond to one of the multiple gantry angles. Each of the multiple image data sub-sets may be reconstructed to obtain an image such that the multiple image data sub-sets may be reconstructed to obtain multiple images. The multiple images may constitute an image sequence (e.g., a 3D image including multiple image slices) corresponding to a time period, which can reflect a global condition of the subject during the time period. For example, during a time period, a CT device may rotate its radiation source by 240 gantry angles to obtain 240 image data sub-sets relating to the heart of the patient. Accordingly, the time period may correspond to an image sequence including 240 images relating to the heart.

During the scan of the subject during the plurality of time periods, the subject may undergo the physiological motion. The physiological motion may include a cardiac motion, a respiratory motion, or the like, or any combination thereof. In some embodiments, the physiological motion may include a motion cycle. Taking the cardiac motion as an example, the cardiac motion may include a cardiac motion cycle. The duration of the cardiac motion cycle may be 0.8 seconds (0.8 s), 1 s, etc. As used herein, a duration of a time period (e.g., each of the plurality of time periods, each of the at least two time periods) may be shorter than the duration of the motion cycle. Merely by way of example, for the duration of the cardiac motion cycle being 1 s, a duration of a time period may be 0.05 s, 0.1 s, 0.2 s, 0.3 s, etc. In some embodiments, as the duration of the time period is relatively short, an image sequence corresponding to a time period may be represented by an image sequence corresponding a time point within the time period (e.g., a start or end time point of the time period, a middle time point of the time period, etc.) for brevity. In some embodiments, a start time point of the scan (or a start point of one of the plurality of time periods) may correspond to any position of a motion cycle. For example, the start time point of one of the plurality of time periods (or scan cycles) may correspond to the start of a motion cycle. That is, the start time point of one of the plurality of time periods may coincide with when a new motion cycle starts. As another example, the start time point of one of the plurality of time periods may correspond to a time point within a motion cycle. That is, the start time point of one of the plurality of time periods falls in the middle of a motion cycle (e.g., ¼ into a motion cycle, the mid-point of a motion cycle, ¾ into a motion cycle, etc.).

In some embodiments, the processing device 120A may obtain a plurality of image sequences each corresponding to one of the plurality of time periods. Each of the plurality of image sequences may be reconstructed based on an image data set acquired during one of the plurality of time periods. An image data set may include multiple image data sub-sets each corresponding to a gantry angle as described elsewhere in the present disclosure. The processing device 120A may determine the at least two image sequences from the plurality of image sequences. The at least two image sequences may include N image sequences. N may be an integer greater than 2 such as 2, 3, 5, 8, 10, 15, or the like. The at least two image sequences may be reconstructed based on image data acquired within a same motion cycle or different motion cycles. In some embodiments, the processing device 120A may determine image sequences that satisfy a preset condition as the at least two image sequences. For example, the processing device 120A may determine, from the plurality of image sequences, image sequences that satisfies a preset image quality as the at least two image sequences. For instance, a motion artifact in each of the at least two image sequences may be less than a preset motion artifact threshold. As another example, the processing device 120A may determine, from the plurality of image sequences, any successive image sequences as the at least two image sequences. That is, the at least two time periods corresponding to the at least two image sequences may be any successive time periods within the plurality of time periods. For instance, the start time point of the scan may be denoted by 0 s for brevity. For the duration of a time period being 0.05 s and N being 3, the at least two time periods may include 3 time periods denoted by 0 s-0.05 s. 0.05 s-0.1 s, and 0.1 s-0.15 s.

As still another example, the processing device 120A may determine a motion amplitude of the subject for each of the plurality of image sequences. The processing device 120A may determine the at least two image sequences based on the motion amplitude of each of the plurality of image sequences. In some embodiments, the processing device 120A may determine a motion amplitude of the subject for a specific image sequence based on adjacent image sequences of the specific image sequences. For example, the processing device 120A may determine a variation of the subject between the specific image sequence and its preceding and/or successive image sequences. As used herein, a preceding image sequence of a specific image sequence refers to an image sequence reconstructed based on an image data set acquired in a time period immediately before the time period when the image data set on the basis of which the specific image sequence is reconstructed is acquired. As used herein, a successive image sequence of a specific image sequence refers to an image sequence reconstructed based on an image data set acquired in a time period immediately after the time period when the image data set on the basis of which the specific image sequence is reconstructed is acquired. The processing device 120A may determine the motion amplitude of the subject for the specific image sequences based on the variation.

In some embodiments, the processing device 120A may obtain physiological motion data (e.g., an ECG image) relating to the subject that is detected during the plurality of time periods. The physiological motion data may reflect the physiological motion of the subject during the plurality of time periods. The processing device 120 may determine the at least two image sequences based on the physiological motion data. For example, for each of the plurality of time periods, the processing device 120A may determine a motion amplitude of the cardiac motion of the heart based on the ECG image relating to the heart. The processing device 120A may determine the at least two time periods from the plurality of time periods based on the plurality of motion amplitudes of the cardiac motion of the heart. For example, the processing device 120A may rank the plurality of motion amplitudes. The processing device 120A may determine the at least two time periods based on at least two minimum motion amplitudes in the plurality of ranked motion amplitudes. As another example, the processing device 120A may determine, from the plurality of motion amplitudes, at least two motion amplitudes each of which is less than a threshold amplitude. The processing device 120A may determine the at least two time periods based on the at least two motion amplitudes. Further, the processing device 120 may obtain, from the plurality of image data sets, at least two image data sets based on the at least two time periods.

Each of the at least two image data sets may be acquired during one of the at least two time periods. The processing device 120 may determine the at least two image sequences by reconstructing the at least two image data sets using a reconstruction algorithm. The reconstruction algorithm may include an iterative reconstruction algorithm (e.g., a statistical reconstruction algorithm), a Fourier slice theorem algorithm, a filtered back projection (FBP) algorithm, a fan-beam reconstruction algorithm, an analytic reconstruction algorithm, or the like, or any combination thereof. Alternatively, the processing device 120A may directly determine, from the plurality of image sequences, the at least two image sequences based on the at least two time periods.

In 503, the processing device 120A (e.g., the generation module 403) may generate, based on the at least two image sequences, at least one corrected image sequence relating to the subject by correcting, using a motion correction model, an artifact caused by the physiological motion.

As used herein, a motion correction model refers to a machine learning model (e.g., a deep learning model) configured for motion artifact correction based on at least two image sequences and time information thereof. In some embodiments, the motion correction model may be a trained deep learning model. Merely by way of example, the motion correction model may include a trained neural network model, such as a trained U-NET model (e.g., a trained residual U-NET model, a trained dense U-NET model), a trained V-NET model, a trained super-resolution convolutional neural network (SRCNN) model, etc.

In some embodiments, the processing device 120A (e.g., the obtaining module 401) may obtain the motion correction model from one or more components of the imaging system 100 (e.g., the storage device 130, the terminals(s) 140) or an external source via a network (e.g., the network 150). For example, the motion correction model may be previously trained by a computing device (e.g., the processing device 120B), and stored in a storage device (e.g., the storage device 130, the storage 220, and/or the storage 390) of the imaging system 100. The processing device 120A may access the storage device and retrieve the motion correction model. In some embodiments, the motion correction model may be generated by a computing device (e.g., the processing device 120B) by performing a process (e.g., process 700) for generating the motion correction model disclosed herein. More descriptions regarding the generation of the motion correction model may be found elsewhere in the present disclosure (e.g., FIG. 7 and relevant description thereof).

In some embodiments, the processing device 120A may determine at least two ranked image sequences by ranking, based on the at least two time periods, the at least two image sequences. The processing device 120A may input the at least two ranked image sequences, according to the ranking of the at least two image sequences, into the motion correction model. The processing device 120A may output the at least one image sequence by the motion correction model.

In some embodiments, the processing device 120A may determine whether the at least two image sequences correspond to a same motion cycle. In response to determining that the at least two image sequences correspond to the same motion cycle, the processing device 120A may directly rank the at least two image sequences according to a chronological order of at least two time periods (e.g., in descending or ascending order). In response to determining that the at least two image sequences do not correspond to a same motion cycle (i.e., the at least two image sequences corresponding to different motion cycles), for each of the plurality of time periods, the processing device 120 may determine a relative position of the time period with respect to its corresponding motion cycle. The processing device 120A may rank the at least two time periods, according to an order (e.g., a descending or ascending order) of the at least two relative positions, based on the at least two relative positions. The processing device 120A may determine the at least two ranked image sequences by ranking, based on the at least two ranked time periods, the at least two image sequences.

Merely by way of example, for a cardiac scan during a plurality of time periods within 0 s-3 s, the duration of the cardiac cycle may be 1 s, and the duration of each of the plurality of time periods may be 0.2 s. The at least two image sequences may include 3 image sequences corresponding to 3 time periods, e.g., 0 s-0.2 s, 1.4 s-1.6 s, and 2.2 s-2.4 s. Assuming that the start point of the cardiac scan corresponds to a start position of a cardiac cycle, the cardiac scan may correspond to 15 motion cycles and the 3 image sequences may correspond to three different motion cycles among the 15 motion cycles. For brevity, each motion cycle may be denoted by 0%-100% where 0% corresponds to a start position of the motion cycle and 100% corresponds to an end position of the motion cycle. Accordingly, a relative position of the time period 0 s-0.2 s with respect to its corresponding motion cycle may be denoted by 0%-20%, a relative position of the time period 1.4 s-1.6 s with respect to its corresponding motion cycle may be denoted by 40%-60%, and a relative position of the time period 2.2 s-2.4 s with respect to its corresponding motion cycle may be denoted by 20%-40%.

Alternatively, the relative position of a time period may be represented by the mid-point of the time period with respect to its motion cycle. For instance, the relative position of the time period 0 s-0.2 s with respect to its corresponding motion cycle may be denoted by 10%, a relative position of the time period 1.4 s-1.6 s with respect to its corresponding motion cycle may be denoted by 50%, and a relative position of the time period 2.2 s-2.4 s with respect to its corresponding motion cycle may be denoted by 30%. The processing device 120A may rank the 3 time periods according to an ascending order or descending order of the 3 relative positions. For instance, the 3 ranked time periods may be in a sequence of 0 s-0.2 s, 2.2 s-2.4 s, and 1.4 s-1.6 s, or a sequence of 1.4 s-1.6 s, 2.2 s-2.4 s, and 0 s-0.2 s. Further, the processing device 120A may rank the 3 image sequences based on the 3 ranked time periods. Further, the processing device 120A may input the 3 ranked image sequences to output at least one corrected image sequence (e.g., a corrected image sequence).

According to some embodiments of the present disclosure, as a physiological motion of a subject (e.g., a tissue or an organ) has a continuity (e.g., a motion cycle), a corrected image sequence relating to a subject may be determined using the motion correction model based on at least two image sequences relating to the subject corresponding to least two time periods. In such situations, the physiological motion of the subject during the at least two time periods may be taken into consideration by inputting the at least two image sequences in an order (e.g., a chronological order) into the motion correction model, which can facilitate the determination of a change of the subject due to the physiological motion (e.g., a motion trajectory of the subject) during the at least two time periods, thereby facilitating the correction of motion artifact in a resultant image caused by the physiological motion according to the physiological motion and a relevant change of the subject due to the physiological motion during the at least two time periods.

In some embodiments, a count (or number) of the at least one corrected image sequence output by the motion correction model may be determined depending on training samples used for training the motion correction model. Each of the training samples may include at least two sample image sequences and at least one gold standard image sequence. That is, a relationship between the count of the at least one corrected image sequence output by the motion correction model and the count of the at least two image sequences input to the motion correction model may be the same as a relationship between a count of the at least one gold standard image sequence and a count of the at least two sample image sequences. For example, the count of the at least one corrected image sequence output by the motion correction model may be the same as the count of the at least one gold standard image sequence included in each training sample used for training the motion correction model. The count of the at least two image sequences may be the same as the count of the at least two sample image sequences included in each training sample used for training the motion correction model. More descriptions regarding the training samples may be found elsewhere in the present disclosure (e.g., FIG. 7 and the description thereof).

In some embodiments, the at least one corrected image sequence may correspond to a specific time period (also referred to as a second time period). For example, the at least one corrected image sequence may include M corrected image sequences. M may be an integer equal to or greater than 1. The M corrected image sequences may correspond to M second time periods. The duration of a second time period may be the same as a duration of a first time period (that corresponds to a ranked image sequence input into the motion correction model). Alternatively, the duration of the second time period may be different from the duration of the first time period. In some embodiments, as the duration of a second time period is relatively short, the at least one corrected image sequence corresponding to the second time period may be represented as at least one corrected image sequence corresponding to a specific time point relating to the second time period (e.g., a start time point, an end time point, or a middle time point of the second time period).

In some embodiments, the at least one second time period corresponding to the at least one corrected image sequence may be determined depending on the training samples used for training the motion correction model. The at least two sample image sequences included in each training sample may correspond to at least two third time periods. The at least one gold standard image sequence included in each training sample may correspond to at least one fourth time period. That is, a relationship between the at least one second time period and the at least two first time periods may be the same as a relationship between the at least one fourth time period corresponding and the at least two third time periods. For example, a count of the at least one second time period may be the same as a count of the at least one fourth time period. The count of the at least two first time periods may be the same as a count of the at least two third time periods. As another example, a relative position of the at least one second time period with respect to the at least two first time periods may be the same as a relative position of the at least one fourth time period with respect to the at least two third time period. For illustration purposes, the following description is provided with reference to at least two image sequences within a motion cycle. For example, the count (or number) of the at least two image sequences may be 2. The two image sequences may correspond to two first time periods denoted by 0 s-0.05 s and 0.05 s-0.1 s. The motion correction model may be trained using the training samples each including two sample image sequences and a gold standard image sequence. The gold standard image sequence may correspond to a fourth time period in the middle of two third time periods corresponding to the two sample image sequences and a duration of the fourth time period may be the same as a duration of a third time period. Accordingly, the at least one corrected image sequence determined by inputting the two image sequences to the motion correction model may include only one corrected image sequence. The only one corrected image sequence may correspond to a second time period in the middle of the two first time periods and the duration of the second time period may be the same as the duration of a first time period, e.g., the second time period being denoted by 0.025 s-0.075 s. Alternatively, the motion correction model may be trained using the training samples each including two sample image sequences and two gold standard image sequences. Each of the two gold standard image sequences may correspond to one of the two sample image sequences. Accordingly, the at least one corrected image sequence determining by inputting the two image sequences to the motion correction model may include two corrected image sequences each of which corresponds to one of the two image sequences. The two corrected image sequences may correspond to two second time periods corresponding to the two first time periods, e.g., the two second time periods being denoted by 0 s-0.05 s and 0.05 s-0.1 s, respectively.

As another example, the count (or number) of the at least two image sequences may be equal to 3, and the three image sequences may correspond to three first time periods denoted by 0 s-0.05 s, 0.05 s-0.1 s, and 0.1 s-0.15 s. The motion correction model may be trained using training samples each including three sample image sequences and a gold standard image sequence. The three sample image sequence may correspond to three third time periods. The gold standard image sequence may correspond to a fourth time period in the middle of the three time periods and a duration of the fourth time period may be the same as a duration of each of the three third time periods. The at least one corrected image sequence determined by inputting the three image sequences into the motion correction model may include only one corrected image sequence. The only one corrected image sequence may correspond to a second time period in the middle of the three first time periods, e.g., the second time period being denoted by 0.05 s-0.1 s.

As still another example, the count (or number) of the at least two image sequences may be equal to 4, and the four image sequences may correspond to four first time periods denoted by 0 s-0.05 s, 0.05 s-0.1 s, 0.1 s-0.15 s, and 0.15 s-0.2 s. The motion correction model may be trained using training samples each including four sample image sequences and two gold standard image sequences. The four sample image sequences may correspond to four third time periods. The two gold standard image sequences may correspond to two fourth time periods each of which within the middle of the three time periods and a duration of a fourth time period may be the same as a duration of a third time period. The at least one corrected image sequence determined by inputting the four image sequences to the motion correction model may include two corrected image sequences. The two corrected image sequences may correspond to two second time periods each of which is within the four first time periods, e.g., the two second time periods being denoted by 0.05 s-0.1 and 0.1 s-0.15 s, respectively. Alternatively, the motion correction model may be trained using training samples each including four sample image sequences and a gold standard image sequence. The four sample image sequences may correspond to four third time periods. The gold standard image sequence may correspond to a fourth time period in the middle of the three time periods and a duration of the fourth time period may be the same as a duration of a third time period. The at least one corrected image sequence determined by inputting the four image sequences to the motion correction model may include only one corrected image sequence corresponding to a second time period in the middle of the four first time periods, e.g., the second time period being denoted by 0.075 s-0.125 s.

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations of the process 500 may be omitted and/or one or more additional operations may be added. For example, a storing operation may be added elsewhere in the process 500. In the storing operation, the processing device 120A may store information and/or data (e.g., the at least one corrected image sequence) used or obtained in other operations of the process 500 in a storage device (e.g., the storage device 130) disclosed elsewhere in the present disclosure. As another example, an additional operation for transmitting the at least one corrected image to a terminal device for display may be added after operation 503. In some embodiments, during the application of the motion correction model, the processing device 120A may input both the at least two image sequences and the at least two time periods to the motion correction model. The processing device 120A may output the at least one corrected image sequence by the motion correction model.

Figure 6:
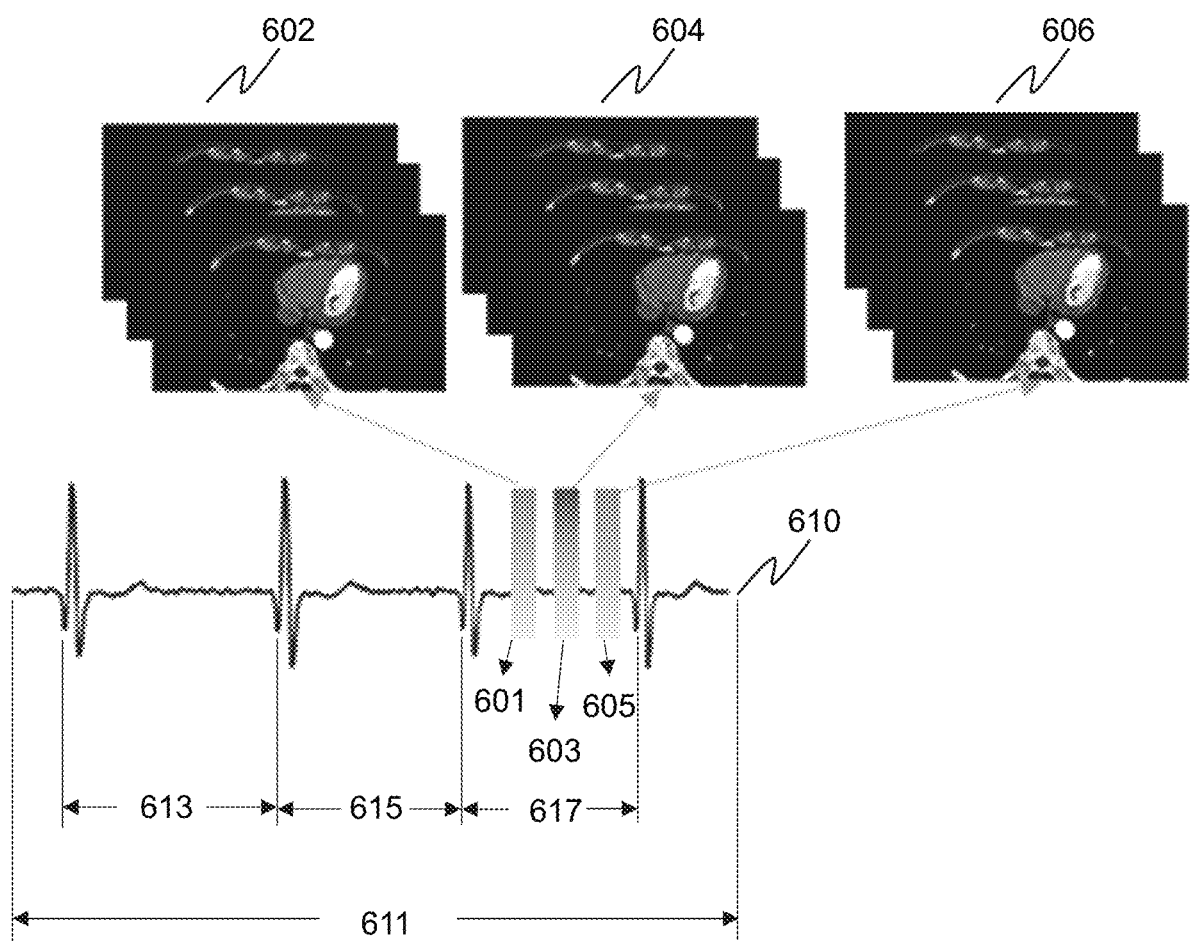
FIG. 6 is a schematic diagram illustrating an exemplary process of determining at least two image sequences according to some embodiments of the present disclosure.

FIG. 6 is a schematic diagram illustrating an exemplary process of determining at least two image sequences according to some embodiments of the present disclosure. The processing device 120A may obtain a plurality image data sets relating to a scan of the heart of a patient (not shown). The plurality of image data sets may be acquired by a medical imaging device (e.g., the medical imaging device 110) during one of a plurality of time periods. The processing device 120A may also obtain an ECG image 610 relating to the heart of the patient. The ECG image 610 may be acquired by a physiological motion detection device (e.g., an ECG monitor device) during the plurality of time periods. According to the ECG image 610, a duration of the scan including the plurality of time periods may be denoted by 611. The heart of the patient may undergo a cardiac motion including three complete cardiac motion cycles (denoted by 613, 615, and 617, respectively). The processing device 120A may determine three time periods (denoted by 601, 603, and 605, respectively) from the plurality of time periods, which is similar to the determination of at least two first time periods as described elsewhere in the present disclosure (e.g., operation 501 and the description thereof). The processing device 120A may determine three image data sets from the plurality of image data sets based on the three time periods. Each of the three image data sets may be acquired during one of the three time periods. The processing device 120A may determine three image sequences corresponding to the three time periods (denoted by 601, 603, and 605, respectively) by reconstructing the three image data sets. Further, the processing device 120A may determine a corrected image sequence (not shown) based on the three image sequences by using a motion correction model as described elsewhere in the present disclosure.

FIG. 7 is a flowchart illustrating an exemplary process for generating a motion correction model according to some embodiments of the present disclosure. In some embodiments, process 700 may be implemented as a set of instructions (e.g., an application) stored in a storage device (e.g., the storage device 130, storage 220, and/or storage 390). The processing device 120B (e.g., the processor 210, the CPU 340, and/or one or more modules illustrated in FIG. 4B) may execute the set of instructions, and when executing the instructions, the processing device 120B may be configured to perform the process 700. The operations of the illustrated process presented below are intended to be illustrative. In some embodiments, the process 700 may be accomplished with one or more additional operations not described and/or without one or more of the operations discussed. Additionally, the order of the operations of process 700 illustrated in FIG. 7 and described below is not intended to be limiting. In some embodiments, the motion correction model described in operation 503 may be obtained according to the process 700. In some embodiments, the process 700 may be performed by another device or system other than the imaging system 100, e.g., a device or system of a vendor of a manufacturer. For illustration purposes, the implementation of the process 700 by the processing device 120B is described as an example.

In 701, the processing device 120B (e.g., the obtaining module 405) may obtain a plurality of training samples. Each of the plurality of training samples may include at least two sample image sequences relating to a sample subject and at least one gold standard image sequence corresponding to the at least two sample image sequences.

As used herein, a sample subject refers to an object whose data is used for training the motion correction model. The sample subjects may meet a certain preset condition. For example, the sample subjects may be of a same gender and/or of similar ages. As another example, the sample subjects may be of the same type of organ, tissue, etc. For instance, the sample subjects may be the hearts of different patients. In some embodiments, the sample subjects may include the subject to be scanned as described in connection with FIG. 5, the description of which is not repeated here. For example, data from the subject to be scanned obtained in one or more prior scans may be used as the training data for training the motion correction mode. That is, a training sample may include at least two prior image sequences of the subject acquired when a prior scan is performed on the subject and at least one gold standard image sequences relating to the subject. The sample subjects may include objects other than the subject to be scanned, e.g., organs from different patients.

The at least two sample image sequences may correspond to at least two sample time periods (also referred to as third time periods). A sample time period may be similar to the first time period as described in FIG. 5, the description of which is not repeated here. For example, the duration of the sample time period may be shorter than a duration of a motion cycle of the sample subject. The duration of the sample time period may range from 0 s-3 s (e.g., 0.05 s, 0.1 s, 0.2 s, 0.3 s, etc.) for a cardiac motion cycle being 1 s. In some embodiments, as the duration of the third time period is relatively short, the third time period may be represented by a time point relating to the third time period, which is similar to the first time period.

As used herein, a sample image sequence relating to the sample subject refers to an image sequence of the sample subject that is reconstructed based on image data of the sample subject acquired by a medical imaging device (e.g., the medical imaging device 110) during one of the at least two sample time periods, which is similar to an image sequence of the subject as described in connection with operation 501. The sample subject may undergo a physiological motion during the at least two sample time periods. In some embodiments, the at least two sample image sequences may be stored in a storage device (e.g., the storage device 130 of the imaging system 100, or an external resource such as a medical institution (e.g., a disease examination center, a hospital, etc.) or an open-source database). The open-source database may include a Github database, an ISBI database, an LIDC-IDRI database, a DDSM MIAS database, a Cancer Imaging Archive database, an OsiriX database, a NITRC database, etc.). The processing device 120B may obtain the at least two sample image sequences from the storage device. Alternatively, the processing device 120B may obtain at least two sample image data sets relating to the sample subject. The processing device 120B may determine the at least two sample image sequences by reconstructing the at least two sample image data sets using a reconstruction algorithm as described elsewhere in the present disclosure.

The at least one gold standard image may correspond to at least one fourth time period. As used herein, a fourth time period may be similar to the second time period as described in FIG. 5, the description of which is not repeated here. For example, the duration of the fourth time period may be the same as or different from the duration of the third time period. As another example, the at least one fourth time period may correspond to at least one of the at least two third time periods. In some embodiments, as the duration of the fourth time period is relatively short, the fourth time period may be represented by a time point relating to the fourth time period, which is similar to the second time period. As used herein, a gold standard image sequence refers to a motion artifact-free image sequence (also referred to as a ground truth image sequence or a labeled image sequence) of the sample subject. Alternatively, the gold standard image sequence may be regarded as having no motion artifact for brevity. For example, the motion artifact-free image sequence may have no detectable artifact caused by the physiological motion according to a standard (e.g., determined by a computing device according to an artifact detection algorithm or a feature recognition algorithm or by an observer). As another example, the motion artifact-free image sequence may have an artifact that is less than a threshold artifact. As another example, the motion artifact-free image sequence may be a corrected image sequence that is determined using a motion correction algorithm. For instance, the processing device 120B may segment the at least two sample image sequences relating to the sample subject. The processing device 120B may determine a motion trajectory of the sample subject by registering the segmented sample image sequences. The processing device 120B may correct the motion artifact based on the determined motion trajectory to generate the at least one gold standard image sequence. In some embodiments, the processing device 120B may obtain the at least one gold standard image sequence from the storage device where the at least two image sequences are obtained.

In some embodiments, a count (or number) of the at least two sample image sequences of each of at least some of the plurality of training samples may be equal to a count (or number) of the at least two image sequences of the subject to be used as an input of a motion correction model trained using the training samples. For example, if the motion correction model is trained using the plurality of training samples each of which includes five sample image sequences, in an application of the motion correction model, 5 image sequences need to be input to the motion correction model. Similarly, a count (or number) of the at least one gold standard image sequences may be equal to the count (or number) of the at least one corrected image sequences of the subject the motion correction model outputs in a specific application. For example, if the motion correction model is trained using the plurality of training samples each of which includes a gold standard image sequence, the motion correction model in a specific application may include one corrected image sequence.

In 703, the processing device 120B (e.g., the training module 407) may generate the motion correction model by training a machine learning model using the plurality of samples.

In some embodiments, the machine learning model may include a deep learning model. The deep learning model may include a neural network model, such as a U-NET model (e.g., a residual U-NET model, a dense U-NET model), a V-NET model, a super-resolution convolutional neural network (SRCNN) model, etc.

In some embodiments, the processing device 120B may divide the plurality of training samples into a first portion and a second portion (e.g., randomly). The first portion may be used to train the machine learning model to obtain the motion correction model. The second portion may be used to test the motion correction model to determine whether the motion correction model is satisfactory. In some embodiments, a ratio of a count (or number) of the first portion and a count (or number) of the second portion may be 8:2, 9:1, 9.5:0.5, etc.

In some embodiments, the machine learning model may include one or more model parameters. The processing device 120B may initialize parameter value(s) of the model parameter(s) before training, and one or more of the value(s) of the model parameter(s) may be updated during the training of the machine learning model. Exemplary model parameters of the preliminary model may include the number (or count) of layers, the number (or count) of kernels, a kernel size, a stride, a padding of each convolutional layer, a loss function, or the like, or any combination thereof.

For illustration purposes, the following description is provided with reference to each training sample including at least two training image sequences and only one gold standard image sequence. In some embodiments, the training of the machine learning model may include one or more iterations. Taking a current iteration of the one or more iterations as an example, the processing device 120B may input at least two sample image sequences of the first portion to an updated machine learning model which is obtained in a previous iteration. The processing device 120B may output a corrected sample image sequence by the updated machine learning model. Further, the processing device 120B may determine an assessment result that indicates the accuracy and/or efficiency of the updated machine learning model.

In some embodiments, the assessment result may be associated with a difference between the corrected sample image sequence and a gold standard image sequence corresponding to the at least two sample image sequences of the first portion. For example, the processing device 120B may determine a loss function to measure the difference. In some embodiments, the assessment result may be associated with the number (or count) of iterations that have been performed. Additionally or alternatively, the assessment result may be associated with the number (or count) of training samples that have been used to train the updated machine learning model. In some embodiments, the assessment result may include a determination of whether a termination condition is satisfied in the current iteration. For example, the termination condition may be deemed satisfied if a value of the loss function is minimal or smaller than a threshold (e.g., a constant). As another example, the termination condition may be deemed satisfied if the value of the loss function converges. In some embodiments, convergence may be deemed to have occurred if, for example, the variation of values of loss functions in two or more consecutive iterations is equal to or smaller than a threshold (e.g., a constant). As still another example, the termination condition may be deemed satisfied if a certain count of iterations that have been performed. As a further example, the termination condition may be deemed satisfied if a certain count of the training samples that have been used.

In some embodiments, in response to determining that the termination condition is satisfied in the current iteration, the processing device 120B may designate the updated machine learning model as a trained machine learning model. In other words, parameters of the updated machine learning model may be designated as parameters of the trained machine learning model. In response to determining that the termination condition is not satisfied, the processing device 120B may update, based on the assessment result, parameter value(s) of the updated machine learning model to be used in a next iteration. Merely by way of example, the processing device 120B may update the parameter value(s) of the updated machine learning model based on the value of the loss function according to, for example, a Backpropagation through time (BPTT) algorithm. In some embodiments, the updated machine learning model may include a plurality of parameter values, and updating parameter value(s) of the updated machine learning model refers to updating at least a portion of the parameter values of the updated machine learning model.

After the trained machine learning model is determined, the processing device 120B may input at least two sample image sequences of each of the second portion into the trained machine learning model. The processing device 120B may output a corrected sample image sequence by the trained machine learning model for the at least two sample image sequences. The processing device 120B may determine whether the corrected sample image sequence is consistent with a gold standard image sequence corresponding to the at least two sample image sequences of the second portion to determine a corresponding testing result. For example, the processing device 120B may determine a similarity value between the corrected sample image sequence and the corresponding gold standard image sequence. The processing device 120B may determine whether the similarity value exceeds a similarity threshold. In response to determining that the similarity value exceeds a similarity threshold, the processing device 120B may determine that the corrected sample image sequence is consistent with the corresponding gold standard image sequence, which indicates the corresponding testing result is positive. Further, the processing device 120B may determine whether an accuracy rate of the trained machine learning model is satisfactory. For example, the processing device 120B may determine a ratio of a count (or number) of positive testing results to the count (or number) of the second portion as the accuracy rate of the trained machine learning model. The processing device 120B may determine whether the accuracy rate is greater than a threshold (e.g., 85%, 90%, 95%, 98%, etc.). In response to a determination that the accuracy rate is greater than the threshold, the processing device 120B may designate the trained machine learning model as the motion correction model. In response to a determination that the accuracy rate is less than the threshold, the processing device 120B may initiate new training iterations (e.g., by selecting another machine learning model and/or using new training samples, etc.).

In some embodiments, the motion correction model may include a trained machine learning model configured to correct motion artifact for image sequences relating to multiple tissues and/or organs (e.g., the heart and the lung). Alternatively, the motion correction model may include a trained machine learning model configured to correct motion artifact for image sequences relating to a specific tissue/organ. For example, the motion correction model may include a motion correction model for the heart, a motion correction model for the lung, etc.

It should be noted that the above description regarding process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added or omitted. For example, the motion correction model may be stored in a storage device (e.g., the storage device 130) disclosed elsewhere in the present disclosure for further use (e.g., in the determination of the at least one corrected image sequence as described in connection with FIG. 5). In some embodiments, the processing device 120B may divide the plurality of training samples into the first portion, the second portion, and a third portion. The third portion may be used to verify the trained machine learning model (e.g., to verify hyper-parameters (e.g., a learning rate) of the trained machine learning model). Then, the second portion may be used to test the verified machine learning model. In some embodiments, the processing device 120B may update the motion correction model periodically or aperiodically based on one or more newly-generated training samples. For example, the processing device 120B may update the motion correction model based on a feedback of the motion correction model when the user uses the motion correction model.

EXAMPLES

The following examples are provided for illustration purposes and not intended to be limiting.

Figure 8:
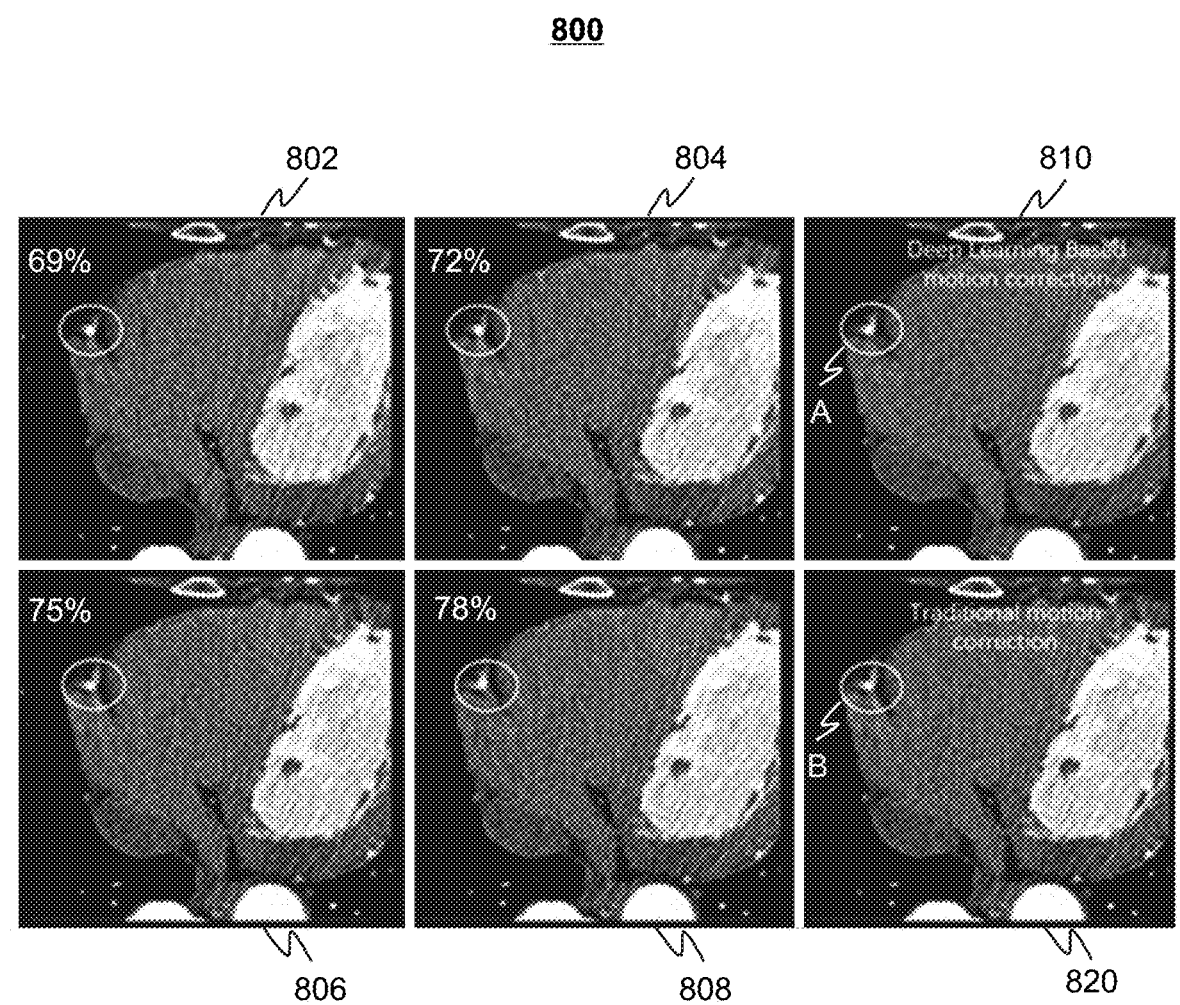
FIG. 8 is a schematic diagram illustrating an example of motion correction according to some embodiments of the present disclosure.

FIG. 8 includes image sequences obtained by image reconstruction of image data acquired using a CT device, and exemplary corrected image sequences. Four image sequences of the heart of a patient acquired using a CT device are denoted by 802, 804, 806, and 808. The four image sequences correspond to four time periods denoted by 69%, 72%, 75%, and 78% of the cardiac motion cycle of the patient. Assuming a duration of a cardiac motion cycle being 1 s and a start time point of the four time periods coinciding with a start position of the cardiac motion cycle, 69% denotes 0.69 s into the cardiac motion cycle, and the image sequence 802 corresponds to a time period denoted by 0.675 s-0.705 s. The four image sequences were input into a motion correction model as described elsewhere in the present disclosure. A corrected image sequence denoted by 810 was output by the motion correction model. A second corrected image sequence denoted by 820 was obtained using a traditional motion correction algorithm based on a motion trajectory of the heart. As shown in FIG. 8, by comparing the corrected image sequence 810 and the second corrected image sequence 820, especially, portion A of the corrected image sequence 810 and portion B of the second corrected image sequence 820, the corrected image sequence 810 indicates a better correction effect than the second corrected image sequence 820.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A non-transitory computer-readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C #, VB. NET, Python or the like, conventional procedural programming languages, such as the "C" programming language, Visual Basic, Fortran, Perl, COBOL, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system for motion correction in medical imaging, comprising:
   at least one storage device including a set of instructions; and
   at least one processor configured to communicate with the at least one storage device, wherein when executing the set of instructions, the at least one processor is configured to direct the system to perform operations including:
      obtaining at least two image sequences relating to a subject, wherein each of the at least two image sequences is reconstructed based on image data that is acquired by rotating a radiation source of a medical imaging device by multiple gantry angles of the medical imaging device during one of at least two time periods, the subject undergoes a physiological motion during the at least two time periods, and the at least two image sequences satisfy a condition relating to a motion amplitude; and
      generating at least one corrected image sequence relating to the subject by inputting the at least two image sequences into a motion correction model for correcting an artifact caused by the physiological motion, wherein the motion correction model is a trained deep learning model, a count of the at least one corrected image sequence is less than a count of the at least two image sequences, and the generating the at least one corrected image sequence relating to the subject by inputting the at least two image sequences into the motion correction model includes:
         determining at least two ranked image sequences by ranking, based on the at least two time periods, the at least two image sequences;
         inputting, according to the ranking of the at least two image sequences, the at least two ranked image sequences into the motion correction model; and
         outputting the at least one corrected image sequence by the motion correction model.

2. The system of claim 1, wherein each of at least two image sequences relates to the heart of the subject, and the physiological motion includes a cardiac motion.

3. The system of claim 1, wherein the physiological motion includes a motion cycle.

4. The system of claim 3, wherein a duration of each of the at least two time periods is shorter than a duration of the motion cycle.

5. The system of claim 3, wherein the at least two image sequences are acquired within a same motion cycle or different motion cycles.

6. The system of claim 1, wherein the obtaining at least two image sequences relating to the subject includes:
obtaining a plurality of image sequences relating to the subject; and
determining the at least two image sequences from the plurality of image sequences.

7. The system of claim 1, wherein
the at least two image sequences are acquired within a same motion cycle, and
the determining at least two ranked image sequences by ranking, based on the at least two time periods, the at least two image sequences includes:
ranking, according to a chronological order of the at least two time periods, the at least two image sequences.

8. The system of claim 1, wherein
the at least two image sequences are acquired within different motion cycles, and
the determining at least two ranked image sequences by ranking, based on the at least two time periods, the at least two image sequences includes:
for each of the at least two time periods, determining a relative position of the time period with respect to its corresponding motion cycle;
ranking, according to an order of the at least two relative positions, the at least two time periods; and
ranking, according to the at least two ranked time periods, the at least two image sequences.

9. The system of claim 1, wherein the motion correction model is obtained according to operations including:
obtaining a plurality of samples each of which includes at least two sample image sequences relating to a sample subject and at least one gold standard image sequence corresponding to the at least two sample image sequences, wherein each of the at least two sample image sequences is reconstructed based on image data acquired by the medical imaging device during one of at least two sample time periods and the at least one gold standard image sequence has no motion artifact; and
generating the motion correction model by training a machine learning model using the plurality of samples.

10. The system of claim 9, wherein the gold standard image sequence is determined by:
segmenting the at least two sample image sequences relating to the sample subject;
determining a motion trajectory of the sample subject by registering the segmented sample image sequences; and
correcting a motion artifact in the at least two sample image sequences based on the motion trajectory to generate the gold standard image sequence.

11. The system of claim 1, wherein one of the at least one corrected image sequence corresponds to a second time period in the middle of the at least two time periods.

12. The system of claim 11, wherein a duration of the second time period is the same as a duration of each of the at least two time periods.

13. A method for motion correction in medical imaging, the method being implemented on a computing device including at least one processor and at least one storage device, the method comprising:
obtaining at least two image sequences relating to a subject, wherein each of the at least two image sequences is reconstructed based on image data that is acquired by rotating a radiation source of a medical imaging device by multiple gantry angles of the medical imaging device during one of at least two time periods, the subject undergoes a physiological motion during the at least two time periods, and the at least two image sequences satisfy a condition relating to a motion amplitude; and
generating at least one corrected image sequence relating to the subject by inputting the at least two image sequences into a motion correction model for correcting an artifact caused by the physiological motion, wherein the motion correction model is a trained deep learning model, a count of the at least one corrected image sequence is less than a count of the at least two image sequences, and the generating the at least one corrected image sequence relating to the subject by inputting the at least two image sequences into the motion correction model includes:
determining at least two ranked image sequences by ranking, based on the at least two time periods, the at least two image sequences;
inputting, according to the ranking of the at least two image sequences, the at least two ranked image sequences into the motion correction model; and
outputting the at least one corrected image sequence by the motion correction model.

14. The method of claim 13, wherein
the at least two image sequences are acquired within a same motion cycle, and
the determining at least two ranked image sequences by ranking, based on the at least two time periods, the at least two image sequences includes:
ranking, according to a chronological order of the at least two time periods, the at least two image sequences.

15. The method of claim 13, wherein
the at least two image sequences are acquired within different motion cycles, and
the determining at least two ranked image sequences by ranking, based on the at least two time periods, the at least two image sequences includes:
for each of the at least two time periods, determining a relative position of the time period with respect to its corresponding motion cycle;
ranking, according to an order of the at least two relative positions, the at least two time periods; and
ranking, according to the at least two ranked time periods, the at least two image sequences.

16. The method of claim 13, wherein the motion correction model is obtained according to operations including:
obtaining a plurality of samples each of which includes at least two sample image sequences relating to a sample subject and at least one gold standard image sequence corresponding to the at least two sample image sequences, wherein each of the at least two sample image sequences is reconstructed based on image data acquired by the medical imaging device during one of at least two sample time periods and the at least one gold standard image sequence has no motion artifact; and generating the motion correction model by training a machine learning model using the plurality of samples.

17. A system for generating a motion correction model, comprising:

at least one storage device including a set of instructions; and at least one processor configured to communicate with the at least one storage device, wherein when executing the set of instructions, the at least one processor is configured to direct the system to perform operations including:

obtaining a plurality of samples each of which includes at least two sample image sequences relating to a sample subject and at least one gold standard image sequence corresponding to the at least two sample image sequences, wherein each of the at least two sample image sequences is reconstructed based on image data acquired by rotating a radiation source of a medical imaging device by multiple gantry angles of the medical imaging device during one of at least two sample time periods, the sample subject undergoes a physiological motion during the at least two sample time periods, and the at least one gold standard image sequence has no artifact caused by the physiological motion and is determined based on the at least two sample image sequences; and generating the motion correction model by training a machine learning model using the plurality of samples, wherein the motion correction model is configured for motion artifact correction by inputting at least two image sequences relating to a subject into the motion correction model to obtain at least one corrected image sequence relating to the subject, a count of the at least one corrected image sequence is less than a count of the at least two image sequences, and the generating the motion correction model by training a machine learning model using the plurality of samples includes:

for each of the plurality of samples, ranking, according to the at least two sample time periods, the at least two sample image sequences; and generating the motion correction model by training the machine learning model using the at least two ranked sample image sequences and the gold standard image sequence corresponding to each of the plurality of samples.

18. The system of claim 17, wherein each of at least two sample image sequences relates to the heart of a sample subject, and the physiological motion includes a cardiac motion.

19. The system of claim 17, wherein the physiological motion includes a motion cycle.

20. The system of claim 19, wherein a duration of each of the at least two sample time periods is shorter than a duration of the motion cycle.

* * * * *